United States Patent [19]

Mueller

[11] Patent Number: 5,066,583
[45] Date of Patent: Nov. 19, 1991

[54] METHOD FOR DISTINGUISHING ALCOHOLICS FROM NON-ALCOHOLICS

[75] Inventor: Gerald C. Mueller, Madison, Wis.

[73] Assignee: Wisconsin Alumni Research Foundation, Madison, Wis.

[21] Appl. No.: 287,821

[22] Filed: Dec. 21, 1988

[51] Int. Cl.$^5$ .................. C12Q 1/02; C12Q 1/34; C12Q 1/44
[52] U.S. Cl. ................... 435/18; 435/19; 435/29; 436/63; 436/71; 436/162; 436/901
[58] Field of Search ............... 435/18, 19, 29; 436/63, 436/71, 162, 901

[56] References Cited

U.S. PATENT DOCUMENTS 4,770,996 9/1988 Tasakoff ..................... 435/18

FOREIGN PATENT DOCUMENTS 0331361 9/1989 European Pat. Off. .

OTHER PUBLICATIONS

Alling et al., *Biochim. Biophys. Acta*, 793, 119–122, 1984.
Kinsky et al., *Biochem. Biophys. Res. Communic.* 162, 788–793, 1989.
Diamond et al., *Proc. Natl. Acad. Sci. USA*, 84, 1413–1416, 1987.
Mueller et al., *Proc. Natl. Acad. Sci. USA*, 85, 9778–9782, 1988.
Wrighton, S. A., Pai, J. K. and Mueller, G. C. (1983) Carcinogenesis 4, 1247–1251.
Pai, J. K., Liebl, E. C., Tettenborn, C. S., Ikegwunonu, F. I. and Mueller, G. C. (1987) Carcinogenesis 8, 173–178.
Tettenborn, C. S. and Mueller, G. C. (1987) Biochem. Biophys. Acta 931, 242–250.
Pai, J. K., Siegel, M. I., Egan, R. W. and Billah, M. M. (1988) Biochem. Biophys. Res. Commun. 150, 355–364.
Tettenborn, C. S. and Mueller, G. C. (1988) Biochem. Biophys. Res. Commun., vol. 155, No. 1.
Alling, C., Gustavsson, L. and Anggard, E. (1983) FEBS Lett. 152, 24–28.

*Primary Examiner*—David A. Saunders
*Attorney, Agent, or Firm*—Quarles & Brady

[57] ABSTRACT

A method for distinguishing an alcoholic person from non-alocholic persons which comprises measuring the potential of lymphocytes from that person to produce phosphatidylenthanol and comparing the results obtained with a standard obtained from the lymphocytes of persons which are known not to be at substantial risk of becoming alcohol dependent which lymphocytes were incubated under identical conditions.

4 Claims, 2 Drawing Sheets

FIG. 1
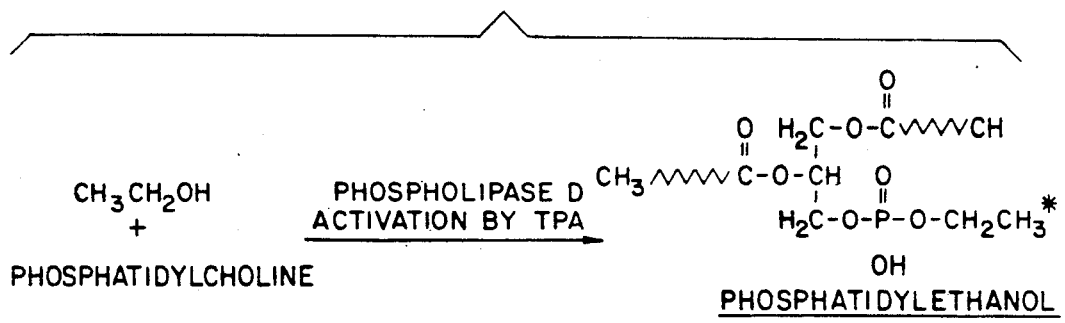
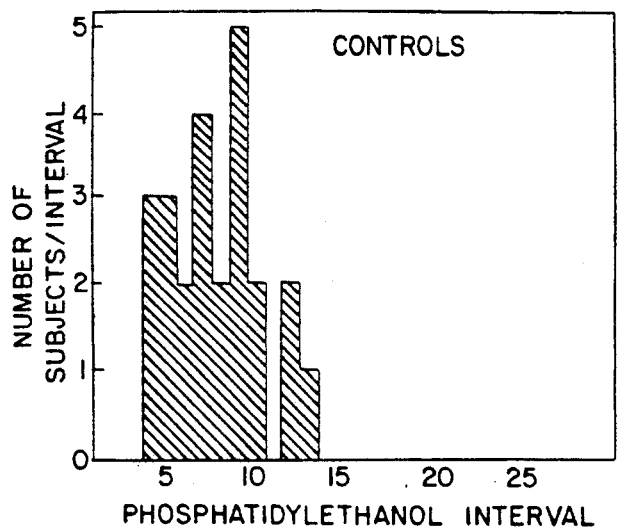
FIG. 3A
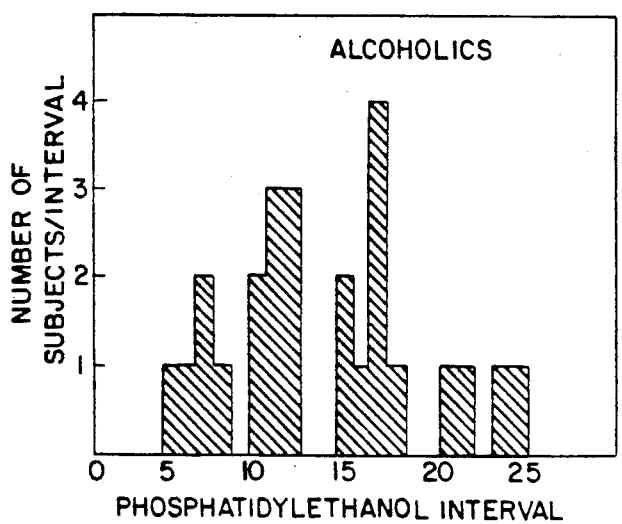
FIG. 3B

METHOD FOR DISTINGUISHING ALCOHOLICS FROM NON-ALCOHOLICS

This invention was made with U.S. government support awarded by the NIH, Grant #: KO6CA00685. The U.S. Government has certain rights in this invention.

FIELD OF THE INVENTION

The present invention generally relates to a method of predicting drug dependency in humans. More particularly, it relates to a method of predicting if an individual has a higher than average risk of becoming alcohol dependent.

BACKGROUND OF THE INVENTION

The tremendous costs of alcohol addiction or dependency to both society and individuals are well documented. It is estimated that the annual cost of alcohol abuse to the U.S. economy exceeds the annual Federal deficit.

At the present time, it is known that some male descendants of alcoholics have a greater potential to become alcohol dependent than the public at large. However, there is not at the present time a method available for predicting which individuals have a higher than average potential for developing alcohol dependency. It is quite likely that if individuals knew with reasonable certainty that they might have a higher than average risk to become alcoholics, they would refrain from consuming all forms of alcohol.

In view of the significant and known adverse effects of alcohol dependency on both society and individuals, it would be advantageous to have a method of predicting who might have a higher than average potential for becoming alcohol dependent.

BRIEF SUMMARY OF THE PRESENT INVENTION

It is the primary object of the present invention to disclose a novel and useful method of predicting if an individual might have a higher than average risk of becoming alcohol dependent.

The method of the present invention basically comprises determining if an individual has a greater potential ability to synthesize phosphatidylethanol than persons who are known not to be alcohol dependent. The method is based on the discovery that the lymphocytes of individuals with an alcohol dependency exhibit an elevated responsiveness to agents which activate the pathway for synthesis of phosphatidylethanol, a unique metabolite of ethanol, which is believed to play a fundamental role in alcohol dependency and associated pathology.

The method comprises taking a blood sample from the individual to be tested; separating the lymphocytes; putting the lymphocytes into tissue culture; exposing them to optimum conditions for phosphatidylethanol synthesis by treating them with ethanol and an activator for the enzyme that catalyzes the synthesis and incubating the mixture; isolating and separating the lipids; determining the level of phosphatidylethanol synthesized and comparing the level against a standard determined by measuring the phosphatidylethanol synthesized by lymphocytes from known non-alcohol dependent individuals incubated in a similar manner. A higher level of phosphatidylethanol in the tested individual than the standard indicates that the individual has a higher than average potential for becoming alcohol dependent.

The results of a pilot study clearly revealed that alcoholics on average had at least two times the potential to synthesize phosphatidylethanol in the assay as did normal non-alcoholic persons. Other findings suggest that phosphatidylethanols may be further metabolized to compounds that covalently react with DNA and that the adducts which form are likely to lead to genetic damage.

BRIEF DESCRIPTION OF THE DRAWINGS

FIG. 1 shows the reaction believed to be involved in the formation of phosphatidylethanol from phosphatidylcholine.

FIG. 3A and 3B are graphs showing the synthesis of phosphatidylethanol by control and alcohol-dependent subjects. The potential for phosphatidylethanol synthesis was measured in control and alcohol-dependent subjects as described under Materials and Methods. Phosphatidylethanol production in this study ranged from 0.42% to 3.91% of the total $^{32}p$-labeled phospholipids; this range of production was divided into 25 equal incremental intervals corresponding to 0.13% of the $^{32}p$-labeled lipid. The number of subjects having phosphatidylethanol production in a given interval is plotted as a histogram for each group of subjects. Control subjects (top panel); Alcoholics (bottom panel).

DESCRIPTION OF THE PREFERRED EMBODIMENT

Figure 2:
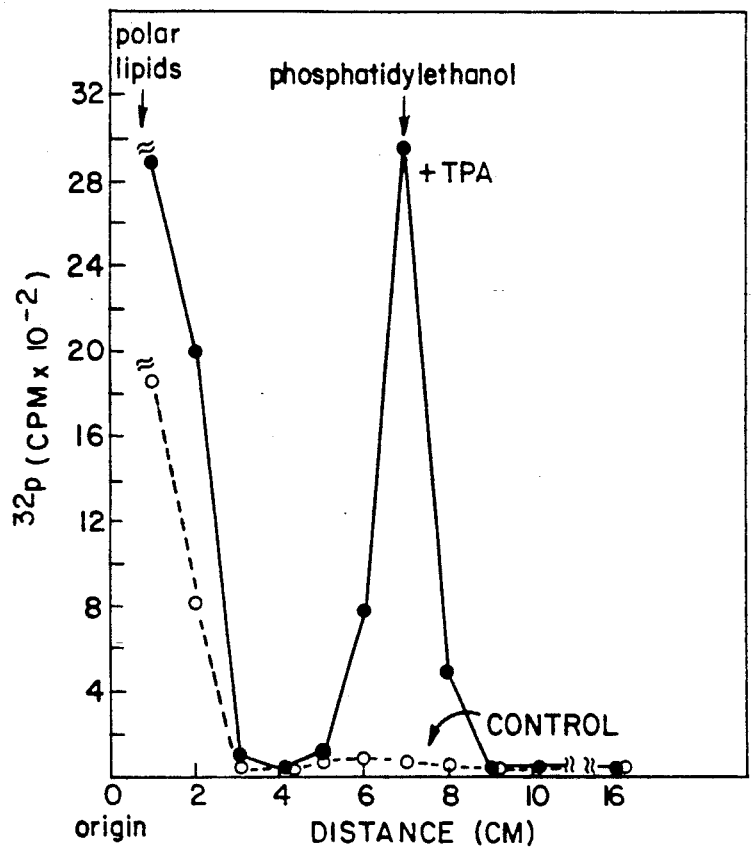
FIG. 2 is a graph showing that TPA induces the synthesis of phosphatidylethanol in human lymphocytes. Lymphocytes ($8.75 \times 10^6$ cells per culture) were prelabeled for 18 hr with $^{32}P$ (20 $\mu ci/ml$). Ethanol (0.5% final concentration) and TPA (100nM) or the control vehicle DMSO were then added and phosphatidylethanol synthesis measured over 180 min. Cell lipids were extracted and resolved by TLC as described under Materials and Methods. The peak of $^{32}p$-labeled lipids in section 6-8 of the chromatogram corresponds to $^{32}p$-phosphatidylethanol. Note the lack of label in this region in the absence of TPA treatment. Control (0); +TPA(•).

In the preferred embodiment, the method involves the collection of blood samples from the test subject in heparin and isolation of the lymphocytes by sedimentation into a ficoll-hypaque density gradient. After washing the white cell layer, the cells are resuspended in Eagle's HeLa medium containing 10% bovine serum at a cell density of $8.75 \times 10^6$ cells/3.5 ml culture. The lipid precursor pools of these cells are then prelabeled for 18 hr with inorganic $^{31}PO_4$ (20 $\mu CI/ml$). After prelabeling, 100 nM TPA is added in DMSO to the cell cultures (final concentration=0.2%) along with exogenous ethanol (final concentration 0.50%); the cells are incubated at 37° C. for an additional 180 minutes. The lipids are extracted with chloroform/methanol (1:1,v/v), taken to dryness in vacuo, and the lipid residues chromatographed on Kodak silica gel chromatographic plates using the organic phase of a mixture containing ethyl acetate, 2,2,4-trimethylpentane, acetic acid, and H$_2$O (110:50:20:100,v/v) as the developing solvent. The phosphatidylethanol and polar lipid regions of the chromatograms are visualized by iodine vapor staining. The appropriate regions of such chromatograms are cut and assayed for $^{32}$P-labeled lipids by liquid scintillation spectrometry. The results are expressed as the percent of $^{32}$P lipid phosphorous that is accounted for as phosphatidyl-ethanol. Control cultures show that negligible levels of phosphatidylethanol-type compounds are synthesized in the absence of either ethanol or TPA treatment. This assay fits the requirement for dependency on cell number, time of incubation, exogenous ethanol, and the concentration of TPA. It has also been used successfully in another study in which sensitivity of breast cancer patients (humans) to tumor promoting agents is being assessed. The results obtained are compared against a standard determined under identical conditions using the lymphocytes of a group of persons known not to be at higher than average risk of developing alcohol dependency. A phosphatidylethanol level higher than the standard indicates the individual has a higher than average risk of developing alcohol dependency (i.e. less than 1 chance in 10,000 of being normal in their ability to deal with alcohol without hazard).

The discovery of the role of phosphatidylethanol in alcoholism could lead to not only the identification of persons at risk, but also the design of therapeutic treatment strategies for persons afflicted with alcoholism and better guidelines for genetic counseling.

Experimental Work

The following is a description of the experimental work that led to the discovery of the method of the present invention.

Phosphatidylethanol, whose synthesis from phospatidylcholine is catalyzed by a phospholipase D in a transphosphatidylation reaction, is a unique metabolite of ethanol. 12-0-Tetradecanoylphorbol-13-acetate, a tumor-promoting phorbol ester and stimulator of protein kinase C, activates this enzyme in peripheral blood lymphocytes. A pilot study of phosphatidylethanol synthesis in lymphocytes of adult males, who have both an alcohol dependency and a family history of alcoholism, has revealed that the average potential for phosphatidylethanol synthesis in this population is significantly elevated over that of control subjects.

In the course of investigating the effects of the tumor-promoting phorbol ester, 12-tetra-decanoylphorbol-13-acetate (TPA) on the metabolism of [$^3$H]arachidonic acid during the mitogenic activation of lymphocytes, Wrighton, Pai, and Mueller (1) discovered that a class of unusual lipid metabolites were rapidly formed in response to TPA. These products were subsequently characterized to be glycerolphospholipids in which the typical head group (i.e., choline, ethanolamine, inositol or serine) had been replaced by ethanol (2)(FIG. 1). The unchanged [$^3$H]arachidonic acid was present as an acyl group in position 1 or 2 of the phospholipid. The formation of this class of acidic lipids, phosphatidylethanols, depended both on the treatment of the cells with an active phorbol ester (or another activator of protein kinase C) and the presence of exogenous ethanol in the culture medium (2,3). Recent studies of Pai et al.(4), and Tettenborn and Mueller (5) have also shown conclusively that the observed phosphatidylethanols are formed by a transphosphatidylation reaction that is catalyzed by membrane-associated phospholipase D; this involves an exchange of ethanol for choline of pre-existing phosphatidylethanol (FIG. 1).

The enzymatic pathway for phosphatidylethanol synthesis appears wide-spread in animal tissues with significant TPA-induced responses being observed in bovine lymphocytes, human peripheral lymphocytes, human mammary cells, human colon cancer cells, and HL-60 cells (2,3). The in vivo production of phosphatidylethanol in kidney, liver, and brain tissues has also been reported independently by Alling and associates (6) for rats receiving toxic doses of ethanol.

The finding, that the pathway for phosphatidylethanol synthesis could be activated by TPA in human lymphocytes from peripheral blood, has opened the way to exploring whether the ability of human subjects to synthesize this unique metabolite of ethanol correlates in any way with the individual's dependency on alcohol. To explore this question, an assay was developed for measuring the induced synthesis of phosphatidylethanol in short-term cultures of human peripheral blood lymphocytes. This test has been used to assess the ability of two groups of males to synthesize phosphatidylethanol: group 1 consists of 24 nonalcoholic males who have no family history of alcoholism in any first degree relatives; and group 2 consists of 25 males who meet the DSM-III (Disease Statistical Manual, version 3, American Psychiatric Association) criteria for alcohol dependence and who also reported an alcoholic parent who meets the DSM-III criteria for abuse and/or dependence (7).

The results of this pilot study show that adult males with both a personal history of alcohol dependence and a family history of alcoholism (DSM-III criteria) have a significantly greater average ability to synthesize phosphatidylethanol than do their control counterparts. These findings provide the first evidence that the synthesis of phosphatidylethanol and the regulation of this phospholipase D-catalyzed pathway can play an important role in alcohol dependency—and may contribute as well to the development of alcohol-related pathology. A molecular and genetic exploration of the components in this pathway is expected to provide new approaches to the therapy and prophylaxis of alcoholism in humans.

MATERIALS AND METHODS

Assay of Potential for Phosphatidylethanol Synthesis using Human Lymphocytes. Approximately 20 ml of venous blood is drawn from the test subject into vacutainer tubes containing 143 USP units of sodium heparin. On mixing with ½ volume of sterile Dulbecco's CA$^{2+}$ and Mg-free phosphate-buffered saline (PBS), 7 ml of the diluted blood is carefully layered over 4 ml of Histopaque-1077(8) in a 15 ml disposable centrifuge tube and centrifuged at 500×g for 30 min. The buffy cell layer is removed and diluted with 25 ml of PBS and the cells pelleted by centrifugation at 350×g for 10 min. The cells are then resuspended in 10 ml of PBS by gentle shaking. A small sample of the suspension is diluted with an equal volume of Eagle's HeLa Medium containing 10% bovine serum and the cell number determined in a hemocytometer. The volume of the cell suspension of PBS, containing the required number of cells, is then sedimented at 300×g for 10 min and the cell pellet resuspended in phosphate-free Eagle's HeLa Medium containing 10% bovine serum at a cell density of 2.5×10$^6$ per ml.

For studies of the induced synthesis of phosphatidylethanol, duplicate 3.5 ml cultures (8.75×10$^6$ cells) were set up in 15 ml screw cap conical glass centrifuge tubes and prelabeled for 18 hr with [$^{32}$P]orthophosphate (20 μCi/ml) by incubation at 37° C. in an atmosphere of 95% air and 5% $CO_2$. TPA (100 nM) in dimethyl sulfoxide (final concentrations, 0.2%), along with ethanol (final concentrations, 0.5%), were then added to the cultures and the incubations continued for 180 min.

Incubations were terminated by sedimenting the cells, washing one time by suspension in 5 ml of cold PBS and initiation of the lipid extraction. The lipid analysis was carried out according to Tettenborn and Mueller (3). The lipids were extracted with chloroform/methanol (1:1, v/v), taken to dryness in vacuo, and the lipid residues chromatographed on plastic-backed silica gel Kodak chromagram TLC plates using the organic phase of a mixture of ethyl acetate, 2,2,4 trimethylpentane, acetic acid, and $H_2O$ (110:50:20:100,v/v) as the developing agent. The phosphatidylethanol and polar lipid regions are visualized by iodine vapor staining and the appropriate regions of the chromatograms are cut and assayed for $^{32}P$-labeled lipids by liquid scintillation spectrometry. The results are expressed as the percent of lipid phosphorus that is accounted for as phosphatidylethanol.

Selection and Classification of Human Subjects. Test subjects for this pilot study were drawn from alcoholic and nonalcoholic adult males ranging in age from 18 to 52 (mean age 34) who utilize an alcohol treatment center (Madison Family Institute or the University of Wisconsin Family Medicine Clinics). The study was limited to males in that the familiar nature of alcoholism, as documented by Goodwin et al. (9), Cotton (10), and Schuckit (11), suggest a male influence in the genetic transmission from parent to offspring. The interviews were conducted by a graduate assistant with experience in conducting alcohol and drug abuse (AODA) assessments. Patients were classified as alcoholic or nonalcoholic by an independent panel of three researchers with experience in AODA using the criteria described below. All classifications were performed by the panel without knowledge of phosphatidylethanol production data. Similarly, the laboratory personnel who performed the assays of induced phosphatidylethanol synthesis were blinded to the alcohol group status of the subjects throughout the assays.

Group 1 consisted of 24 nonalcoholic males who had no history of alcoholism in any first degree relatives. They ranged in age from 20 to 48 years (mean age = 34); 23 subjects were white and nonsmokers. Alcohol consumption in the six months prior to the study ranged from 0 to 21 drinks per week (mean = 4.4). Group 2 consisted of 25 males who met the DSM-III criteria for alcohol dependence and who reported an alcoholic male parent who met DSM-III criteria for abuse and/or dependence. They ranged in age from 18 to 52 years (mean age = 34); all subjects were white, and 4 of the 25 subjects were nonsmokers. Alcohol consumption in the six moths prior to the study ranged from 0 to 189 drinks per week (mean = 81.4).

Materials. The following special reagents were purchased commercially: Histopaque-1077 from Sigma Chemical Company, St. Louis, MO; TPA from IC Services, Woburn, MA; dimethylsulfoxide from Aldrich Chemical Co., Milwaukee, Wis.; and [$^{32}$P]orthophosphate, carrier free, from NEN.

RESULTS

Properties of the Assay System. The enzymatic pathway assayed in this study involves a transphosphatidylation reaction catalyzed by phospholipase D as depicted in FIG. 1. Recent studies of Pai et al. (4) and Tettenborn and Mueller (3,5) have revealed that phosphatidylethanol is the primary donor substrate in the TPA-stimulated system and that a variety of simple alcohols in addition to ethanol can function as the acceptor. This enzymatic pathway also appears to reside in an inactive or cryptic state until activated by an exogenous agent. Phorbol esters that are active as tumor promoters, teleocidin, and bryostatin—all agents that activate protein kinase C—are highly effective stimulators of the in vivo system. In addition, phospholipase D has been shown to be activatable by the chemotactic peptide, N-formyl-Met-Leu-Phe (4), vasopressin (12), and the G-protein activating nucleotide, GTP-γ-S,(5,12).

In the assay used in the present study, the lymphocytes have been cultured for 18 hr in the presence of $^{32}P$ inorganic phosphate to prelabel the pools of phospholipids. To initiate the assay, TPA (100nM) along with 0.5% ethanol are added to the prelabeled cells and the production of phosphatidylethanol was measured after a 180 min incubation period. The TPA and ethanol levels were chosen to give a maximal response in lymphocytes. A typical thin layer chromatogram of the lipid products of control and TPA-treated lymphocytes is shown in FIG. 2. In the absence of TPA, the cells failed to make a measurable level of phosphatidylethanol. Exogenous ethanol was also absolutely required for phosphatidylethanol production (date not shown). The total yield of phosphatidylethanol was also directly proportional to the level of the cells in the culture.

Assay of the Ability of Alcoholic and Nonalcoholic Subjects to Synthesize Phosphatidylethanol. The results of a pilot study are revealed in FIG. 3. In this study, the TPA responses ranged from 0.4 to 4.0% of the lipid phosphorus being accounted for as phosphatidylethanol. For purposes of plotting the data, the full range of phosphatidylethanol production by all subjects was divided into 25 equal intervals; each interval corresponded to a 0.13% increment in the amount of total lipid phosphorus which could be accounted for as phosphatidylethanol; the lowest production interval was 0.42 to 0.55% and the highest interval was 3.78 to 3.91%. The number of subjects of each group that fell into the indicated intervals is plotted as a histogram.

Figure 4:
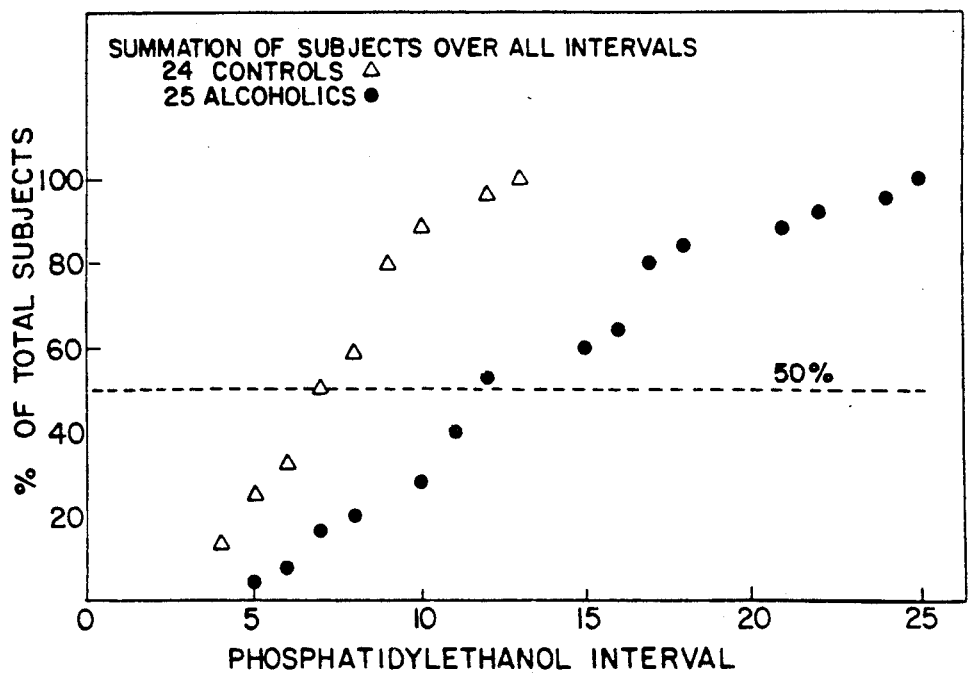
FIG. 4 is a chart showing the percent of total control and alcohol-dependent subjects accounted for with increasing intervals of phosphatidylethanol production. Patients from FIG. 3 have been summed according to their increasing abilities to produce phosphatidylethanol and plotted as accumulation curves. Control subjects (∇); Alcoholics (•).

Inspection of this chart reveals that 23 of the 24 nonalcoholic subjects are clustered in intervals 4 to 12. By contrast, 12 of the 25 alcoholic subjects exhibited potentials for phosphatidylethanol production in intervals 15 to 25, a production range that was above all nonalcoholics. The striking difference in the distribution of these two populations is better visualized when the data are plotted as the percent of test subjects accounted for with increasing levels of phosphatidylethanol production (FIG. 4).

A comparison of the two groups, using the two-sided Wilcoxon rank sum test (13), revealed that phosphatidylethanol production by the alcoholics (mean 2.26% ± 0.77% of $^{32}$Pi-labeled lipids) was significantly greater than among the controls (mean = 1.44% ± 0.37%)(p = <0.0001). As might be expected from the classification determinants, the alcoholics also consumed significantly more alcohol (mean=81±62 drinks per week) than the controls (means=4.4±5.2 drinks per week)(p= <0.0001). The two groups, however, did not differ significantly in age distribution (p= <0.87).

The sensitivity (100-percent of false negatives) and specificity (100-percent of false positives) of the phosphatidylethanol production test were determined using a cut off score of 1.81 (interval 10). In this calculation, the 8 out of 25 alcoholic subjects which registered phosphatidylethanol production levels below the cut off score corresponds to a false negative rate of 32% and a sensitivity of 68%. In the control group of nonalcoholic males, the 3 out of 24 subjects with levels above 1.81, corresponds to a false positive rate of 12% and a sensitivity of 88%.

With respect to the alcoholic subjects whose phosphatidylethanol production potential overlaps the levels exhibited by the controls (i.e., intervals 4 to 12), it can be added that recent experiments have revealed that phosphatidylethanol is also subject to a unique metabolism in certain cell systems. This metabolism is carried out by a steroid-inducible pathway and yields chemically reactive derivatives of phosphatidylethanol. Phosphatidylethanol levels appear to be depressed in cells when this pathway is super-induced, thus the inducible processes may be important to the regulation of phosphatidylethanol levels under the conditions of endogenous stimulation. Since this new pathway could also play a role in the development of alcohol-related pathology as a result of genetic damage to cells, it will be of interest to assess this pathway in control and alcoholic subjects in the near future. Perhaps this analysis will provide the new perspectives that are required for discrimination between the alcoholic and non-alcoholic populations in the region of overlap.

Status of Other Correlations. While the number of test subjects is too small to permit a detailed assessment of other variables that will have to be addressed subsequently in a larger survey, it can be projected that subject age and recent alcohol consumption may not be important parameters. Using Kendall's rank correlation test (13), it was found that phosphatidylethanol production did not vary significantly with age or alcohol consumption (phosphatidylethanol vs age; p=0.09 for controls and 0.81 for alcoholics) (phosphatidylethanol vs alcohol consumption; p=0.28 for controls and 0.61 for alcoholics).

Smoking, however, remains as a potential confounding variable since practically all of the alcoholics were heavy smokers (2 packs of cigaretts/day) whereas the controls were largely nonsmokers. While there is no sound scientific reason for anticipating that smoking contributed to the results, an assessment of this potential confounding variable requires an expansion of the study to include properly matched populations.

DISCUSSION

The results of this pilot study provide strong support for the view that adult males with both a personal and a family history of alcohol dependence have, in general, a higher potential to synthesize phosphatidylethanol—a unique metabolite of ethanol. In fact, the average level of phosphatidylethanol production in TPA-treated lymphocytes of alcoholic subjects was approximately twice that of the control population. Since this synthesis is mediated by an enzyme, phospholipase D, this relationship raises several interesting possibilities: 1. that alcoholics may have a different phospholipase D in their lymphocytes than nonalcoholics—one which is on average twice as active per unit of enzyme protein; 2. that cells of alcoholics contain the same enzyme but carry, on the average, twice the level in a cryptic state; or 3. that the cells of alcoholics have a system for down regulation of phospholipase D activity that is only one half as effective as that of control subjects. To explore these possibilities, as well as others, it will be necessary to isolate phospholipase D and study its regulations using molecular genetic approaches in properly matched sets of family members for each class of subjects. Such studies are expected to establish whether or not there is a fundamental genetic basis for the present results.

The observation that phosphatidylethanol is not synthesized until the cells are exposed to the phorbol ester, suggests that the enzyme resides in a cryptic state—awaiting activation by an exogenous or endogenous factor. Accordingly, a study of the levels of potential activators of phospholipase D, as well as the responsiveness of this enzyme in the cells of control and alcoholic subjects will be of considerable interest. The remarkable responsiveness of the system to phorbol esters, implying that protein kinase C is a major regulator of this pathway, points to a need to assess the role of certain nutrients, growth factors, drugs, and hormones (i.e., agents that mediate their effects through protein kinase C) in alcoholism. This view is also supported by the observation that bryostatin and teleocidin, also activators of protein kinase C, can stimulate this pathway in other cell systems (2,3).

In addition to being regulated directly or indirectly by protein kinase C, the pathway also appears to be responsive to factors that interact with cell surface receptors and propagate their effects through GTP-binding proteins. For example, Bocckino et al. (11) found that vasopressin stimulates phospholipase D in hepatocyte preparations from rat liver. They also showed that this cell surface peptide receptor mechanism could be by-passed in hepatocyte fragments by GTP-$\gamma$-S, a non-hydrolyzable GTP analog that can activate G protein systems. In our own laboratory Tettenborn and Mueller (unpublished data) have shown the activation of phosphatidylethanol production in lysates of H-60 cells by GTP-$\gamma$-S. In a similar type of study, Pai et al. (4) showed that N-formyl-Met-Leu-Phe, a chemotactic peptide produced a rapid, but transitory activation of phospholipase D in macrophages arising from the differentiation of HL-60 cells. These observations, like those showing the role of protein kinase C in the regulation of this pathway, point to the need of screening neuropeptide and related factors in the present system and for possible effects that may relate to the alcoholism problem.

The present pilot study has employed peripheral blood lymphocytes, with an aim to establishing a relatively noninvasive assay for testing the status of human subjects for possible risk for alcoholism. It seems appropriate in the near future to extend the studies and epidemiological correlations to other tissues. In view of the remarkable responsiveness of the system to phorbol esters and the knowledge that these agents work through the activation of the protein kinase C class of enzymes, it will be of interest to assess the level of the different protein kinase C isozymes since they vary remarkably in different tissues and have different phosphorylation targets. Perhaps additional perspectives on the correlations between phosphatidylethanol production and risk status for alcoholism will emerge with such studies. In addition, a correlation of levels of different receptor systems for peptide hormones, adrenergic agents, and growth factors with the responsiveness of the phosphatidylethanol synthesis pathway in such cells, is considered a high priority objective in future studies.

In summary, the studies of phosphatidylethanol synthesis by phospholipase D and the regulatory systems that govern the activity and responsiveness of the enzyme system in control and alcohol-dependent subjects provide a new scientific basis for assessing factors which are relevant to the problem of alcoholism. The new data are of value in identifying subjects at risk, in guiding the genetic counseling, and in the development of new effective therapies for alcohol dependent subjects.

It will be readily apparent to those skilled in the art that the description of the invention has been for purposes of illustration and that other means of measuring an individual's potential for synthesis of phosphatidylethanol may be employed without departing from the spirit and scope of the invention. Therefore, it is intended that the invention not be limited except by the claims.

REFERENCES

1. Wrighton, S. A., Pai, J.-K., and Mueller, G. C. (1983) Carcinogenesis 4, 1247-1251.
2. Pai, J.-K., Liebl, E. C., Tettenborn, C. S., Ikegwuonu, F. I., and Mueller, G. C. (1987) Carcinogenesis 8, 173-178.
3. Tettenborn, C. S., and Mueller, G. C. (1987) Biochem. Biophys, Acta 931, 242-250.
4. Pai, J.-K., Siegel, M./I., Egan, R. W., and Billah, M./M. (1988) Biochem. Biophys. Res. Commun. 150, 355-364.
5. Tettenborn, C. S., and Mueller, G./C. (1988) Biochem. Biophys. Res. Commun., in press.
6. Alling, C., Gustavsson, L., and Anggard, E (1983) FEBS Lett. 152, 24-28.
7. Diagnostic and Statistical Manual of Mental Disorders, p. 165-174, American Psychiatric Association, Washington, D.C. (1986).
8. Loos, J./A., and Roos, D. (1974) Exptl. Cell. Res. 86, 333-341.
9. Goodwin, D. W., Schulsinger, F., and Hermansen, 1. (1973) Arch. Gen. Psychiatry 28, 238-243.
10. Cotton, N. S. (1979) J. Stud. Alcohol 40, 89-116.
11. Schuckit, M. A., (1984) Arch. Gen. Psychiatry 41, 879-884.
12. Bocckino, S. B., Blackmore, P./F., Wilson, P. B., and Exton, J./H. (1987) J. Biol. Chem. 262, 15309-15315.
13. Hollander, M., and Wolfe, D./A. Nonparametic Statistical Methods, John Wiley and Sons, New York, 1973.

I claim:

1. A method of determining if a person is alcohol dependent, which method comprises:
   (a) determining under optimum conditions the ability of the lymphocytes of the person to synthesize phosphatidylethanol; and
   (b) comparing the results obtained against a standard determined under identical conditions employing the lymphocytes of persons known not to be alcohol dependent, whereby a phosphatidylethanol level higher than the standard indicates the person may be alcohol dependent.

2. A method of determining if a person may be alcohol dependent which comprises:
   (a) taking a blood sample from said person and separating the lymphocytes from said sample;
   (b) putting said lymphocytes into tissue culture;
   (c) treating the lymphocytes with ethanol, and an activator for the enzyme catalyzing the synthesis of phosphatidylethanol and incubating the resulting mixture;
   (d) measuring the amount of phosphatidylethanol in the mixture which was synthesized by the lymphocytes; and
   (e) comparing the amount of phosphatidylethanol obtained in (d) against a standard determined by measuring under identical conditions the amount of phosphatidylethanol synthesized by the lymphocytes of persons known not to be alcohol dependent under identical conditions as (c), whereby a higher level of phosphatidylethanol than the standard indicates that said person may be alcohol dependent.

3. A method of claim 2 in which the phosphatidylethanol synthesized is measured by isolating all the phospholipids and separating the different lipids by chromatography.

4. A method of determining if a person may be alcohol dependent which comprises:
   (a) taking a blood sample from said person and isolating the lymphocytes;
   (b) growing the lymphocytes in tissue culture;
   (c) labeling the phospholipid precursors to phosphatidylethanol in said lymphocytes;
   (d) incubating the lymphocytes with ethanol and an activator which promotes the synthesis of phosphatidylethanol;
   (e) isolating the phospholipids from the cells and separating them;
   (f) determining the level of phosphatidylethanol synthesized by the lymphocytes by measuring the labeled phospholipids; and
   (g) comparing said level of phosphatidylethanol obtained to a standard obtained by an identical procedure from the lymphocytes of persons known not to be alcohol dependent and incubated under the same conditions, whereby a phosphatidylethanol level obtained by culturing the lymphocytes of said person which is higher than the standard indicates said person may be alcohol dependent.

* * * * *